United States Patent
Edwardsen et al.

(10) Patent No.: US 6,494,843 B2
(45) Date of Patent: Dec. 17, 2002

(54) TRANSESOPHAGEAL ULTRASOUND PROBE WITH EXPANDABLE SCANHEAD

(75) Inventors: Stephen Dodge Edwardsen, Sandefjord; Jon Ronander, Tonsberg, both of (NO)

(73) Assignee: GE Medical Systems Global Technology Company, LLC, Waukesha, WI (US)

(*) Notice: Subject to any disclaimer, the term of this patent is extended or adjusted under 35 U.S.C. 154(b) by 0 days.

(21) Appl. No.: 09/741,255

(22) Filed: Dec. 19, 2000

(65) Prior Publication Data
US 2002/0077552 A1 Jun. 20, 2002

(51) Int. Cl.[7] .................................. A61B 8/00
(52) U.S. Cl. ..................................... 600/463
(58) Field of Search ........................... 600/437, 439, 600/438, 447, 459, 462–467

(56) References Cited

U.S. PATENT DOCUMENTS

| | | | | |
|---|---|---|---|---|
| 4,794,931 A | * | 1/1989 | Yock ........................... | 600/439 |
| 5,178,150 A | * | 1/1993 | Silverstein et al. .......... | 600/463 |
| 5,190,046 A | * | 3/1993 | Shturman .................... | 600/439 |
| 5,456,258 A | * | 10/1995 | Kondo et al. ............... | 600/463 |
| 5,513,639 A | * | 5/1996 | Satomi et al. .............. | 600/446 |
| 5,699,805 A | * | 12/1997 | Seward et al. .............. | 600/463 |
| 5,752,518 A | * | 5/1998 | McGee et al. .............. | 600/463 |

* cited by examiner

Primary Examiner—Francis J. Jaworski
(74) Attorney, Agent, or Firm—McAndrews, Held & Malloy, Ltd.; Peter J. Vogel; Michael A. Dellapenna (57) ABSTRACT

An internal imaging probe including an expandable scanhead for improving the positioning of an imaging element mounted on the scanhead. The imaging probe is introduced into the esophagus of a patient via the patient's mouth. Once, the imaging probe is introduced, the imaging probe is positioned to a point where an internal structure of the patient is within the direction of view of an imaging element, such as a transducer, located on the scanhead. Once positioned, the scanhead is expanded either by inflation, or via a moving extensor located within the scanhead. The scanhead is then expanded until the imaging element, such as a transducer, achieves close and uniform contact with the esophageal wall of the patient thereby providing accurate imaging of the internal structure. Further, expanding the scanhead while the scanhead is within the esophagus of the patient minimizes the risks of damage to the esophageal wall that are associated with prior art probes. Once the imaging process is complete, the imaging probe is returned to its unexpanded size and removed from the esophagus of the patient. The imaging probe may be included within a medical imaging system that includes the probe, a processing unit, and a monitor for viewing images of the internal structure.

38 Claims, 6 Drawing Sheets

TRANSESOPHAGEAL ULTRASOUND PROBE WITH EXPANDABLE SCANHEAD

BACKGROUND OF THE INVENTION

The present invention generally relates to improvements in a transesophageal ultrasound probe, and more particularly to a transesophageal ultrasound probe including an expandable scanhead.

Various medical conditions affect internal organs and structures. Efficient diagnosis and treatment of these conditions typically require a physician to directly observe a patient's internal organs and structures. For example, diagnosis of various heart ailments often requires a cardiologist to directly observe affected areas of a patient's heart. Instead of more intrusive surgical techniques, ultrasound imaging is often utilized to directly observe images of a patient's internal organs and structures.

Transesophageal Echocardiography (TEE) is one approach to observing a patient's heart through the use of an ultrasound transducer. TEE typically includes a probe, a processing unit, and a monitor. The probe is connected to the processing unit which in turn is connected to the monitor. In operation, the processing unit sends a triggering signal to the probe. The probe then emits ultrasonic signals into the patient's heart. The probe then detects echoes of the previously emitted ultrasonic signals. Then, The probe sends the detected signals to the processing unit which converts the signals into images. The images are then displayed on the monitor. The probe typically includes a semi-flexible endoscope that includes a transducer located near the end of the endoscope.

Typically, during TEE, the endoscope is introduced into the mouth of a patient and positioned in the patient's esophagus. The endoscope is then positioned so that the transducer is in a position to facilitate heart imaging. That is, the endoscope is positioned so that the heart or other internal structure to be imaged is in the direction of view of the transducer. Typically, the transducer sends ultrasonic signals through the esophageal wall that come into contact with the heart or other internal structures.

The transducer then receives the ultrasonic signals as they bounce back from various points within the internal structures of the patient. The transducer then sends the received signals back through the endoscope typically via wiring. After the signals travel through the endoscope, the signals enter the processing unit typically via wires connecting the endoscope to the processing unit.

In order to obtain accurate images of internal organs and structures, such as the heart, it is preferable that the transducer maintain uniform and close contact with the esophageal wall. The close and uniform contact with the esophageal wall typically assists the transducer to receive signals that are minimally distorted.

Figure 1:
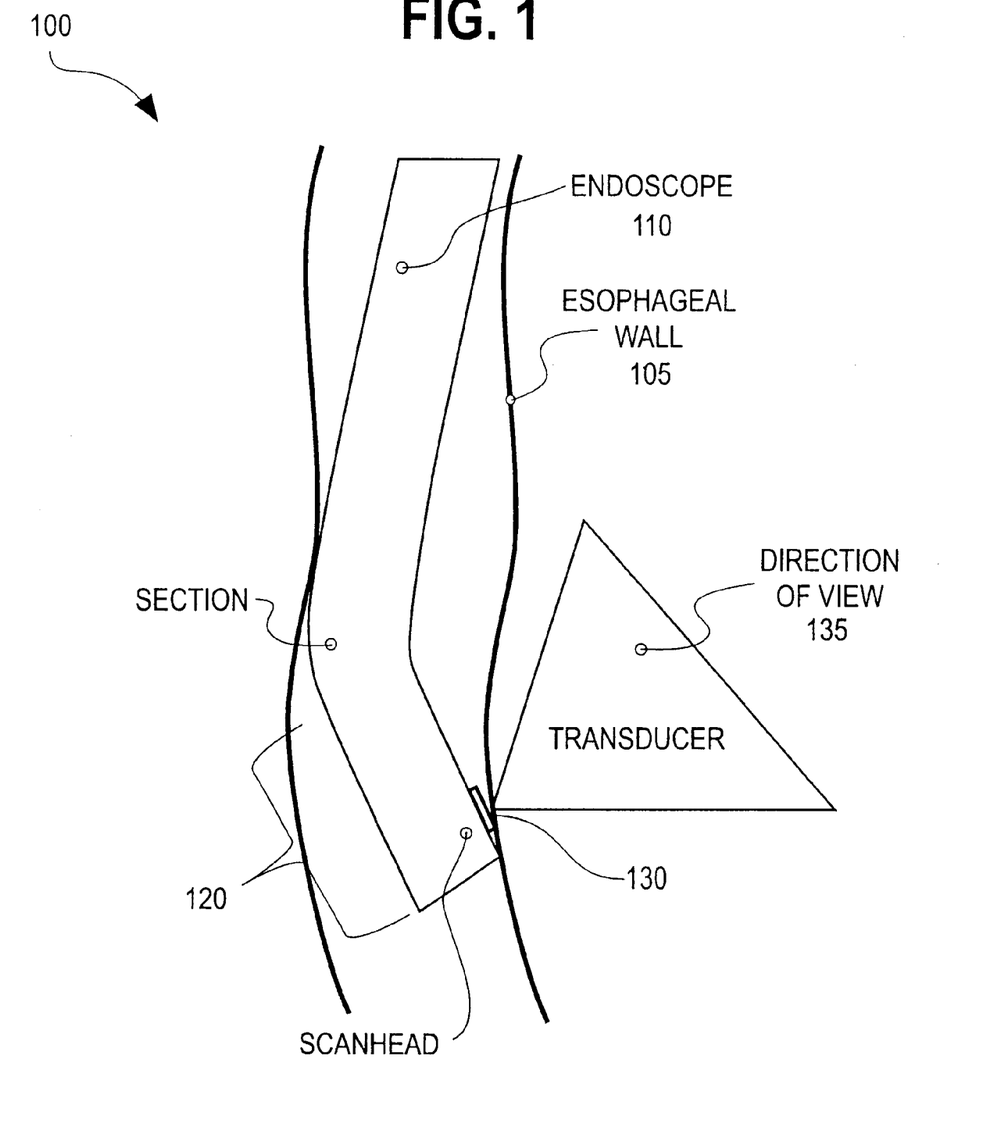
FIG. 1 illustrates a conventional transesophageal probe according to one embodiment of the prior art.

FIG. 1 illustrates a conventional transesophageal probe 100 according to one embodiment of the prior art. The conventional probe 100 includes an endoscope 110 and a control handle (not shown). The enodscope 110 includes a scanhead 120 that includes a transducer 130 mounted on the scanhead 120. The transducer 130 includes a direction of view 135. The transducer 130 comes into contact with an esophageal wall 105 of a patient. The control handle and the scanhead 120 are located at opposite ends of the endoscope 110. The transducer 130 is connected to the processing unit via wiring (not shown) that extends through the scanhead 120 and throughout the length of the body of the endoscope 110. The wiring in the conventional probe 100 is then connected via a cable (not shown) to a processing unit (not shown). The processing unit is then connected via wiring to a monitor (not shown) for display of the ultrasound image.

In operation, the scanhead 120 of the probe 100 is introduced into the esophagus of a patient. The probe 100 is then positioned via the control handle so that the internal structure to be imaged is within the direction of view 135 of the transducer 130. The endoscope 110 of the probe 100 is bent in order to gain leverage so that the transducer 130 located on the scanhead 120 may achieve close and uniform contact with the esophageal wall 110. That is, the endoscope 110 is wedged into the esophageal wall 105. Wedging the endoscope 110 into the esophageal wall of the patient may cause discomfort to the patient and/or injure the patient's esophageal wall. In order to maintain close and uniform contact between the transducer 130 and the esophageal wall 105, the side of the endoscope 110 opposite of the transducer 130 is wedged against one side of the esophageal wall 105 thus pressing the transducer 130 side of the endoscope 110 firmly against the side of the esophageal wall 105 closest to the internal structure being imaged. The transducer 130 then sends ultrasonic signals into the internal structures of the patient and receives the ultrasonic signals that bounce back from the internal structures of the patient. The transducer 130 then sends the ultrasonic signals via wiring through the endoscope 110 to the processing unit. The processing unit then processes and converts the signals into viewable images which are then displayed on the monitor. Once imaging is complete, the endoscope 110 is removed from the patient's esophagus.

Typically, bending the endoscope 110 and wedging the endoscope 110 into the esophageal wall 105 may not be preferable for several reasons. The bending of the endoscope 110 forces the scanhead 120 to engage the esophageal wall at an angle which may negatively impact the transducer's 130 ability to image the internal structure. That is, the operative surface of the transducer 130 on the scanhead 120 is not parallel with the esophageal wall. Instead, the transducer 130 is angled into the esophageal wall. Therefore, the transducer 130 typically is not positioned parallel to the surface of the esophageal wall. Typically, the endoscope 110 is positioned so that the direction of view 135 of the transducer 130 is angled below the structure, or at an acute angle. That is, the direction of view 135 is not at a 90° angle with respect to the structure being imaged. When the direction of view 135 of the transducer 130 is not at a 90° angle with respect to the internal structure being imaged, the image may be distorted due to misleading transducer recordings. That is, the transducer 130 receives signals that bounce back off internal structures that may be at different distances from the transducer 130 if the direction of view 135 was at a 90° with respect to the internal structure. Thus, because the transducer 130 is not parallel and in contact with the esophageal wall 105, the transducer 130 may receive a distorted image.

That is, because the scanhead 120 is angled into the esophageal wall 105, the transducer 130 is typically in partial contact with the esophageal wall. Thus, only the portion of transducer 130 contacting the esophageal wall 105 sends signals to, and receives signals from the internal structure being imaged. The partial contact between the transducer 130 and the esophageal wall 105 typically results in the transducer 130 sending and receiving signals with a low amplification. Consequently, the images generated from the received signals are typically incomplete, attenuated, and/or distorted. Typically, incomplete, attenuated, and/or distorted signals are undesirable for accurate medical diagnosis because the image itself is not an accurate portrayal of the internal structure being imaged.

Further, the direction of view 135 of the transducer 130 may cause the endoscope 110 to be mistakenly positioned due to counter-intuitive images displayed on the monitor. That is, the endoscope 110 is positioned via a control handle located on the probe. The control handle is located at the opposite end of the endoscope 110 as the transducer 130. The endoscope 110 is deflected and bent via the control handle of the probe so that the transducer 130 is tilted upward. Because the transducer 130 is located at the distal end of the endoscope 110, the transducer 130 is titled upward as the endoscope 110 wedges against the esophageal wall 105. Because the transducer 130 images the internal structure from below, the corresponding image sent to the monitor is typically counter-intuitive and can potentially cause confusion to an operator observing the image.

Bending the end of the endoscope 110 so that the transducer 130 is pressed against the esophageal wall 105 of a patient may present various physiological problems as well. For example, moving the bent endoscope 110 further down the esophagus may damage the esophageal wall. That is, because the endoscope 110 is wedged into the esophageal wall 105, the distal end of the endoscope 110 is also wedged into the esophageal wall 105. The distal end of the endoscope 110 may snag the esophageal wall 105 and dig into it thereby damaging the esophageal wall 135.

Further, the force to maintain close and uniform contact between the transducer 130 and the esophageal wall 105 may cause wounds to the esophageal wall 105. That is, because the endoscope 110 is deflected and the transducer 130 is pressed against the esophageal wall 105, the force required to maintain close contact with the esophageal wall 105 may be enough force to lacerate, bruise, or otherwise injure the esophageal wall 105.

Therefore, a need has existed for a transesophageal probe that safely, efficiently and accurately images internal organs and structures. Further, a need has existed for an a transesophageal probe that minimizes the susceptibility of injury to the esophageal wall during procedures such as TEE. A need has also existed for a transesophageal probe that requires less force to. maintain a close and uniform contact between the transducer and the esophageal wall.

BRIEF SUMMARY OF THE INVENTION

An internal imaging probe including an expandable scanhead for improving the positioning of an imaging element mounted on the scanhead. The imaging probe is introduced into the esophagus of a patient via the patient's mouth. Once, the imaging probe is introduced, the imaging probe is positioned to a point where an internal structure of the patient is within the direction of view of an imaging element, such as a transducer, located on the scanhead. Once positioned, the scanhead is expanded. The scanhead may be expanded via inflation, or through the use of a movable extensor located within the scanhead. The inflatable scanhead includes a flexible pouch that receives fluid, such as air or water, from an inflation duct. The scanhead is expanded via engaging a control handle at the proximal end of the imaging probe. Alternatively, the scanhead may be expanded via a moving extensor located within the scanhead. The extensor may be a rotating extensor or a piston-driven extensor.

The scanhead is expanded until the imaging element, such as a transducer, achieves close and uniform contact with the esophageal wall of the patient. Close and uniform contact between the imaging element and the esophageal wall increases the accuracy of the signals received by the imaging element. Further, expanding the scanhead while the scanhead is within the esophagus of the patient minimizes the risks of damage to the esophageal wall that are associated with prior art probes. Once the imaging process is complete, the imaging probe is returned to its unexpanded size and removed from the esophagus of the patient. The imaging probe may be included within a medical imaging system that includes the probe, a processing unit, and a monitor for displaying images of the internal structure.

DETAILED DESCRIPTION OF THE INVENTION

Figure 2:
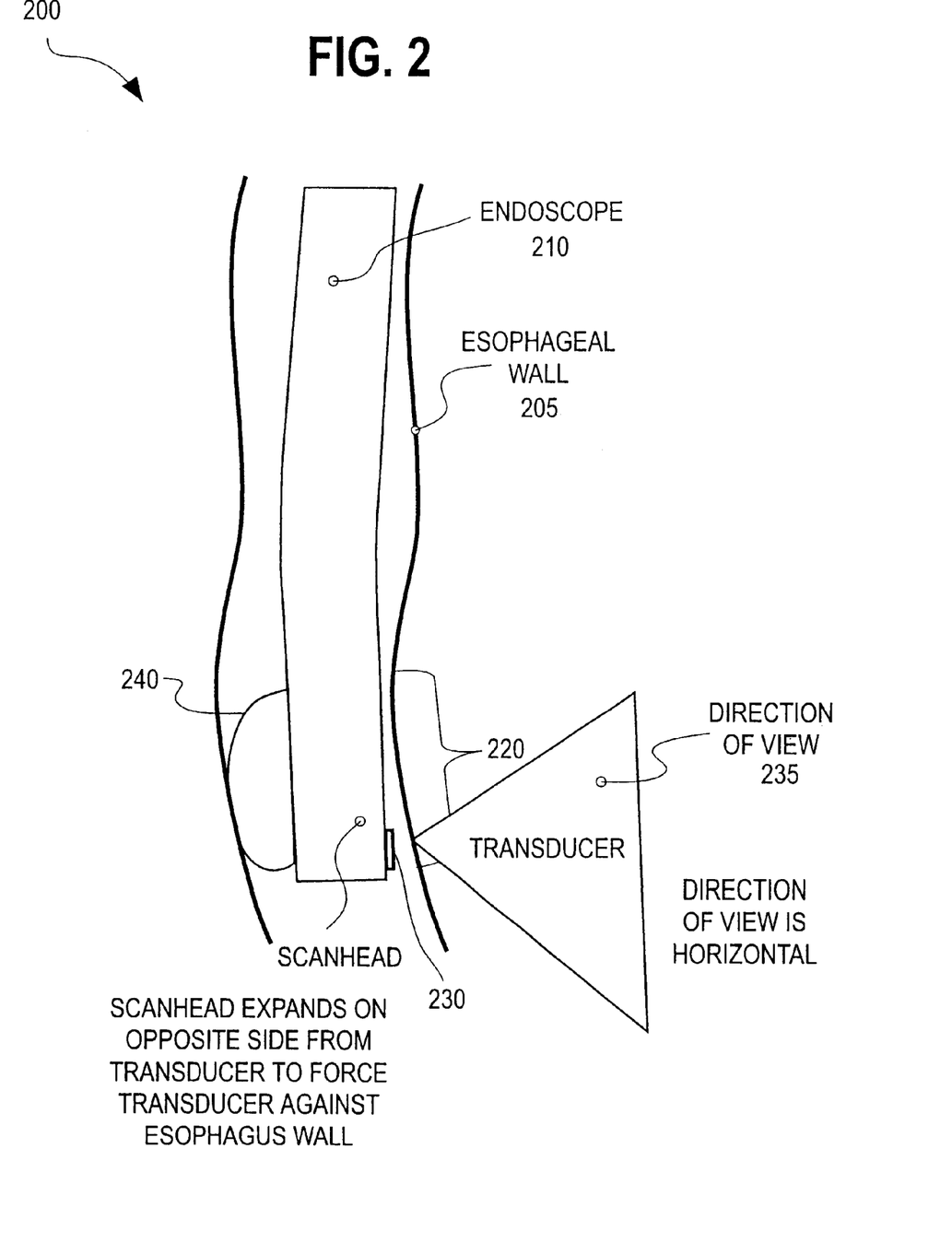
FIG. 2 illustrates a transesophageal ultrasound probe according to a preferred embodiment of the present invention.

FIG. 2 illustrates a transesophageal ultrasound probe 200 according to a preferred embodiment of the present invention. The probe 200 includes a semi-flexible endoscope 210 and a control handle (not shown). The endoscope 210 includes a scanhead 220 which includes a transducer 230, an inflation duct (not shown) connected to the control handle, and a flexible pouch 240. The transducer 230 includes a direction of view 235. The transducer 230 comes into contact with an esophageal wall 205 of a patient. The flexible pouch 240 and the transducer 230 are located on opposite sides of the scanhead 220. The flexible pouch 240 is fixed permanently to the scanhead 220. The flexible pouch is preferably composed of a durable and elastic material, such as Thermo Plastic Elastomer (TPE), that does not pose safety hazards if ingested.

In general, the probe 200 may be included in a medical imaging system. Such a medical imaging system may include the probe 200, a processing unit (not shown), and a monitor (not shown). In operation, an internal structure is imaged by the probe 200 and the resultant image is sent to the processing unit for processing and display on the monitor.

In operation, the probe 200 is introduced into the patient's esophagus via the patient's mouth in a similar fashion as that of the conventional probe 100 of FIG. 1. However, the endoscope 210 of the probe 200 remains relatively straight during positioning and viewing while in the patient's esophagus. Instead of wedging the transducer 230 into the patient's esophageal wall 205, the flexible pouch 240 is inflated to provide close and uniform contact between the transducer 230 and the esophageal wall 205.

First, the endoscope 210 is introduced into the esophagus of a patient. The scanhead 230 is deflated while the endoscope 210 is introduced. Next, the endoscope 210 is positioned so that structure to be imaged is within the direction of view 235 of the transducer 230. The endoscope 210 is positioned so that the direction of view 235 of the transducer is not at an undesired angle with respect to the structure to be imaged. That is, the direction of view 235 of the transducer is preferably at a 90° angle with respect to the internal structure to be imaged. However, the operator may choose to vary the angle somewhat in order to view the structure from different perspectives.

Once the transducer 230 is positioned so that the direction of view 235 is at a 90° angle with respect to the internal structure to be imaged, the flexible pouch 240 is inflated as further described below with respect to FIGS. 3 and 4. The flexible pouch 240 is inflated, or expanded, until the flexible pouch 240 contacts one side of esophageal wall 205. Inflating the flexible pouch 240 moves the transducer 230 into close and uniform contact with the other side of the esophageal wall 205. Once the flexible pouch 240 has been inflated, the transducer 230 is employed to image the desired internal structure. After imaging is complete, the flexible pouch 240 is fully deflated. Once the flexible pouch 240 is fully deflated, the endoscope 210 is removed from the esophagus of the patient.

Because the flexible pouch 240 is relatively soft as compared to the endoscope 210, the risk of damage to the patient is considerably less than that posed by the prior art probe 100. That is, because the preferred embodiment does not require wedging the endoscope 210 into the esophageal wall 205 in order to position the scanhead 220 thereby pressing the angled scanhead 220 into the esophageal wall 205, the risk of an outer edge of the scanhead 220 snagging and damaging the esophageal wall 205 is diminished. Therefore, the endoscope 210 of the present invention may be moved and repositioned during imaging without posing the risks associated with the manual manipulation of the prior art probe 100.

Further, because the scanhead 220 inflates while inside the patient's sophagus, less force is needed to maintain close and uniform contact with the esophageal wall 205 than in the conventional probe 100. That is, the probe 200 does not require the endoscope 210 to wedge into the esophageal wall 205 thereby pressing the distal end of the scanhead 220 into the opposite esophageal wall 205. Rather, the scanhead 220 inflates until both sides of the scanhead 220 contact the esophageal wall 205 while the end of the scanhead 220 remains suspended in the esophagus in an approximately vertical orientation. Because the distal end of the endoscope 210 may be approximately vertical while the imaging process is proceeding, the direction of view 235 of the transducer 230 may be perpendicular to the esophageal wall 205 while imaging internal structures. The probe 200 inflates and provides uniform and close contact with the esophagus wall, but does not require the application of varying degrees of force via manual manipulation to maintain a close and uniform contact between the transducer 230 and the esophageal wall.

Also, because the transducer may be positioned so that the surface of the transducer 230 is parallel to the esophageal wall 205, a larger portion of the transducer 230 may be in direct contact with the esophageal wall 205. Direct contact between the transducer 230 and the esophageal wall 205 is necessary to obtain complete and undistorted images of the internal structure being imaged. Additionally, because the transducer 230 may be positioned so that the direction of view 235 is at a 90° angle with respect to the internal structure being imaged, the accuracy of the imaging of the internal structure may be increased. That is, the transducer 230 may receive signals that more accurately reflect the positions of various points within the internal structure thereby providing more accurate and intuitive images of the internal structure on the monitor. Further, minimal transmission distance between the transducer 230 and the internal structure being imaged decreases the effects of interference.

Figure 3:
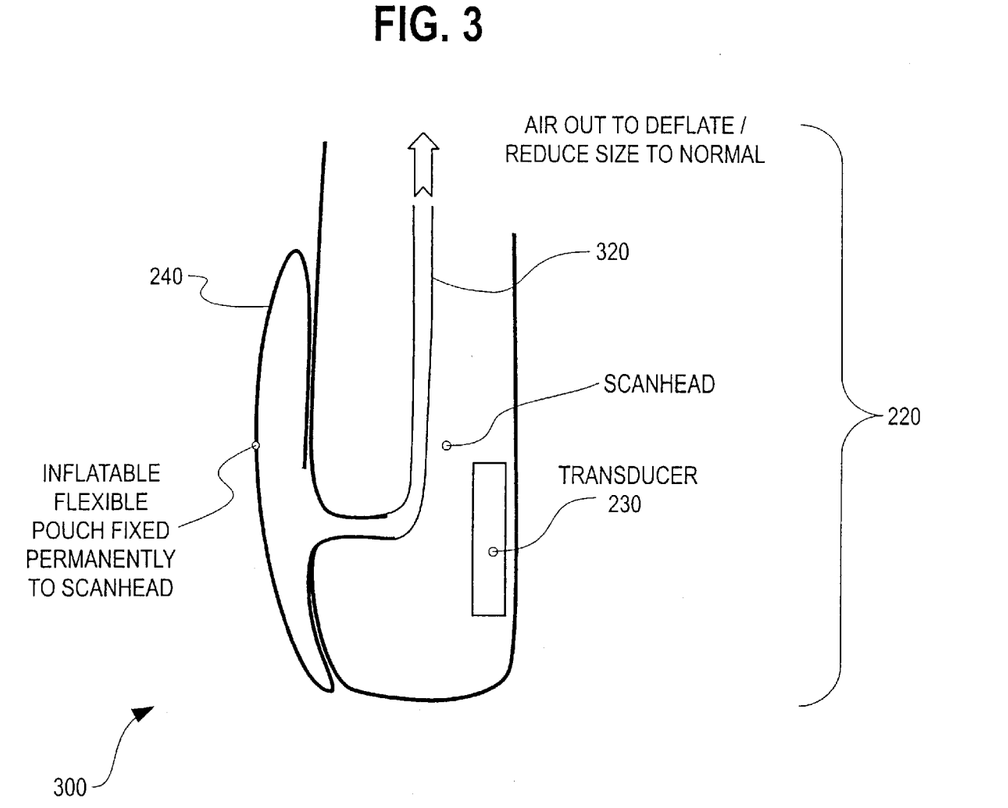
FIG. 3 illustrates a schematic diagram of the operative end of the probe with the flexible pouch deflated according to a preferred embodiment of the present invention.

FIG. 3 illustrates a schematic diagram 300 of the operative end of the probe with the flexible pouch 240 deflated according to a preferred embodiment of the present invention. The schematic diagram 300 includes the scanhead 220 of the endoscope 210 of FIG. 2. The scanhead 220 includes the flexible pouch 240, the transducer 230, and an inflation duct 320. The inflation duct 320 allows fluid, such as a liquid or gas, to flow between the flexible pouch 240 and the control handle (not shown). Preferably, the inflation duct 320 is located inside of the scanhead 220. As discussed above with respect to FIG. 2, the flexible pouch 240 is fixed permanently to the scanhead 220. The flexible pouch 240 and the transducer 230 are located on opposite sides of the scanhead 220 of the endoscope 210. As will be illustrated below with respect to FIG. 4, the flexible pouch 240 inflates or reduces to normal size via the transfer of fluid between the inflation duct 320 and the flexible pouch 240. Conversely, the flexible pouch deflates by releasing fluid from the flexible pouch 240 into the inflation duct 320.

Figure 4:
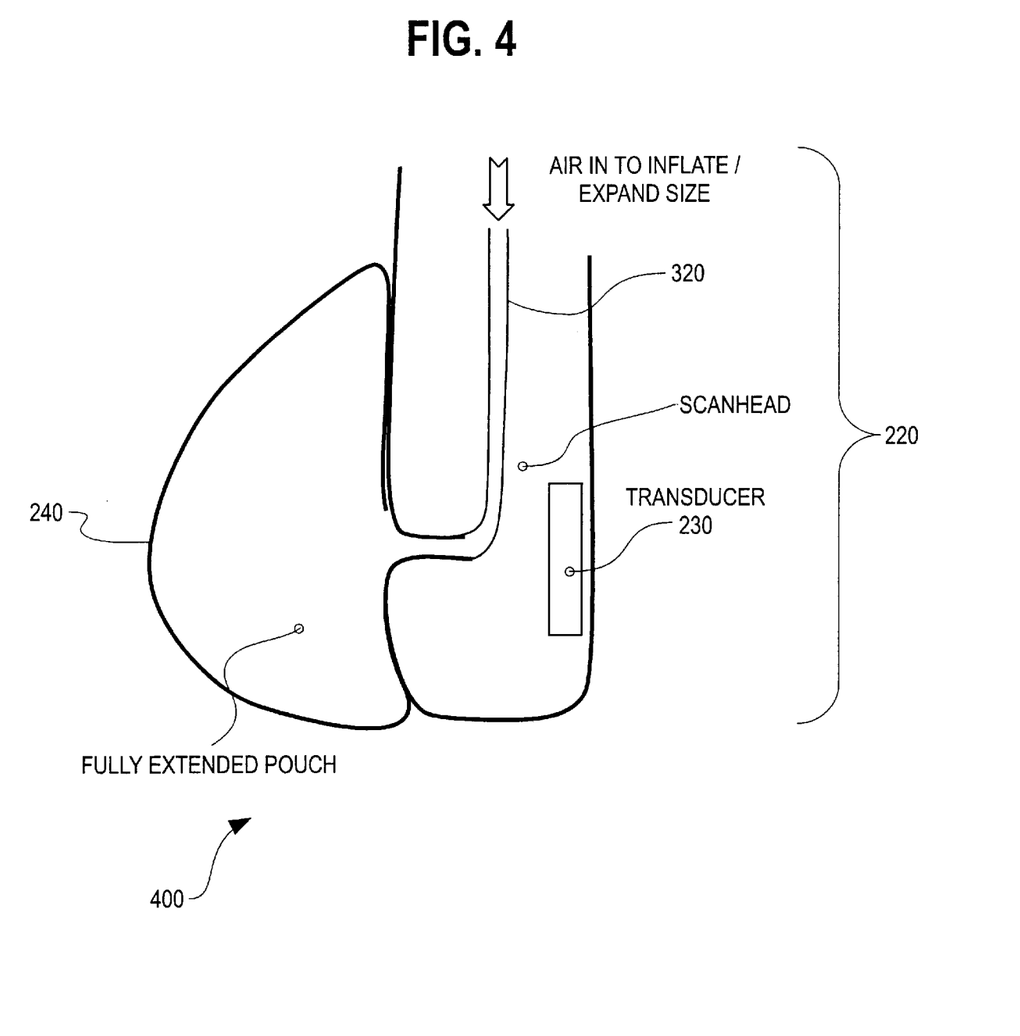
FIG. 4 illustrates a schematic diagram of the operative end of the probe with the flexible pouch inflated according to a preferred embodiment of the present invention.

FIG. 4 illustrates a schematic diagram 400 of the operative end of the probe with the flexible pouch 240 inflated according to a preferred embodiment of the present invention. In order to inflate the scanhead 220, fluid is pumped into the flexible pouch 240 via the inflation duct 320 from a pump in the endoscope handle (not shown). The pump may be a manual pump, such as an air pump of a sphygmomanometer, or the pump may be fully automatic, such as a mechanical air compressor. Fluid, such as air or water, travels from the pump on the control handle into the inflation duct 320. The fluid then travels through the inflation duct 320 until it reaches the flexible pouch 240 where it is stored. The flexible pouch 240 inflates, thereby expanding, as fluid is introduced into the flexible pouch 240.

In order to deflate the flexible pouch 240, the user may release the fluid through a release valve located on the control handle (not shown). Activating the release valve allows fluid to escape from the flexible pouch 240 into the inflation duct 320.

Alternatively, the fluid used to inflate the flexible pouch 240 may be water, another non-toxic liquid, or a gas that poses no safety threats if ingested. Also, alternatively, during deflation, the fluid may be transferred to a different portion of the probe or the fluid may be released into the environment outside of the patient.

Also, the fluid may be evacuated from the inflation duct 320 and the flexible pouch through the use of a fluid suction mechanism.

Also alternatively, the endoscope 210 may include a sealed chamber connected to the flexible pouch 240. Instead of receiving fluid from an external source, the alternative embodiment inflates the flexible pouch 240 by moving fluid stored in the chamber into the flexible pouch 240. The flexible pouch 240 may then be deflated by moving fluid back into the sealed chamber from the flexible pouch 240. Thus, the inflation duct 240 may not be necessary. For example, air may initially be equally distributed throughout a chamber within the endoscope 210. In order to inflate the flexible pouch 240, the control handle may be engaged to alter the distribution of air throughout the chamber. A piston, for example, may be used to move within the chamber thereby compressing the fluid and pushing it toward the scanhead 220 and into the flexible pouch 240. That is, as the piston moves down toward the distal end of the endoscope 210, it pushes the air down toward the distal end of the endoscope 210 into the flexible pouch 240. That is, air, or another fluid, stored within the chamber of the endoscope 210 may be transferred to the flexible pouch 240 of the scanhead 220. In order to deflate the flexible pouch 240, control handle of the probe may be engaged to redistribute the fluid approximately evenly throughout the chamber of the endoscope 210. In other words, the piston may recede back toward the proximal end of the endoscope 210 thereby permitting the fluid to reenter the chamber.

Alternatively, the entire inner chamber of the probe 200 may be used to transfer air to the flexible pouch 240. Instead of using a piston to transfer the air, the probe 200 itself may be pressurized so that force applied to the handle may cause fluid contained within the internal chamber of the probe to migrate to the flexible pouch 240.

The preferred embodiment of the present invention as described in FIGS. 2–4 above employs an inflatable flexible pouch 240 to expand the scanhead 220.

Alternatively, the scanhead 220 of the endoscope 210 may be expanded through the use of a rotating or piston driven extensor located within the scanhead 220 as shown below with respect to FIGS. 5 and 6.

Figure 5:
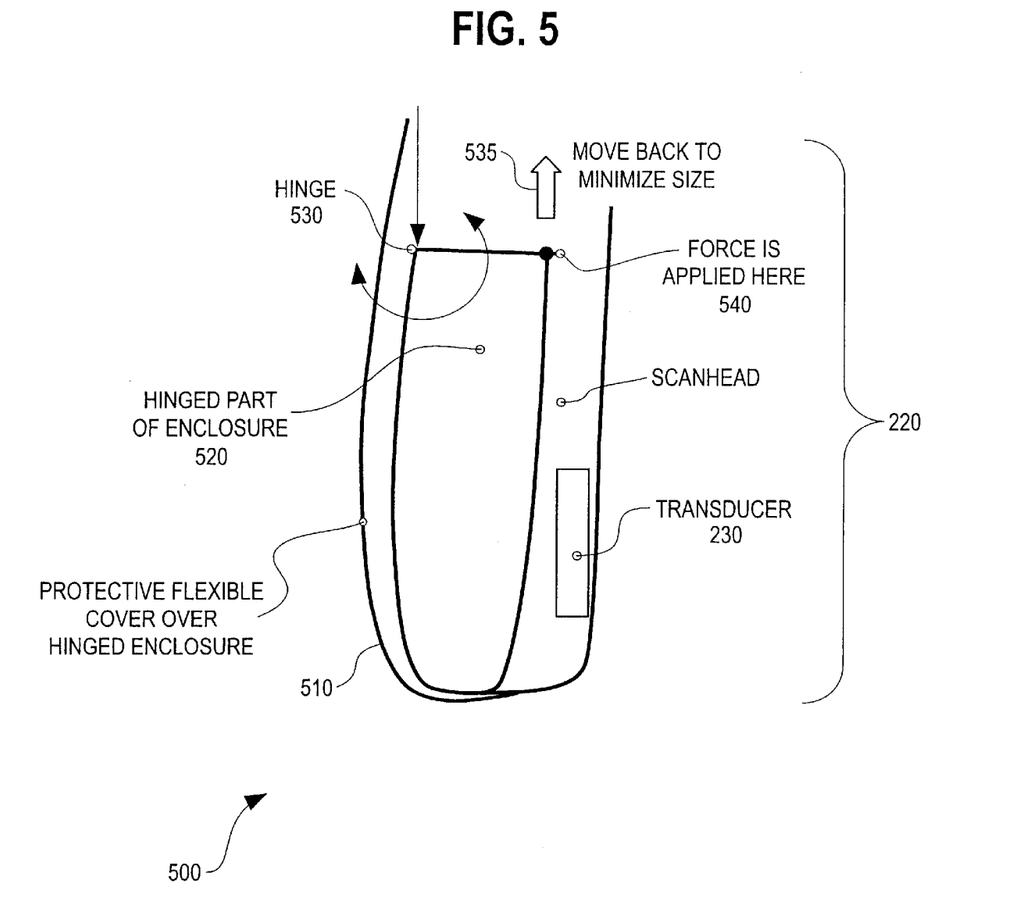
FIG. 5 illustrates a schematic diagram of the operative end of the probe with the scanhead unexpanded according to an alternative embodiment of the present invention.

FIG. 5 illustrates a schematic diagram 500 of the operative end of the probe with the scanhead 220 unexpanded according to an alternative embodiment of the present invention. The schematic diagram 500 includes the scanhead 220 located at the end of the endoscope 210. The scanhead 220 includes the transducer 230, a flexible cover 510, a rotating extensor 520, a hinge 530, an engaging shaft 535, and a force application point 540.

The rotating extensor 520 is located within the scanhead 220 and is connected to the main body of the endoscope 210 at the hinge 530 and at the force application point 540. At the force application point 540, the endoscope is connected to the rotating extensor 520 by the engaging shaft 535. The transducer 230 and the flexible cover 510 are located at opposite sides of the scanhead 220. The flexible cover 510 is connected to the main body of the endoscope 210 and the bottom of the scanhead 220. The flexible cover 510 protects against any possible corners or edges that may be contained within the scanhead 220. Additionally, the flexible cover 510 is airtight. Therefore, because the flexible cover is airtight, it has no holes through which fluids may enter or escape. Consequently, the scanhead 220 may be disinfected quickly and easily because the internal structures of the scanhead 520 are fully contained and protected within the scanhead 220.

Figure 6:
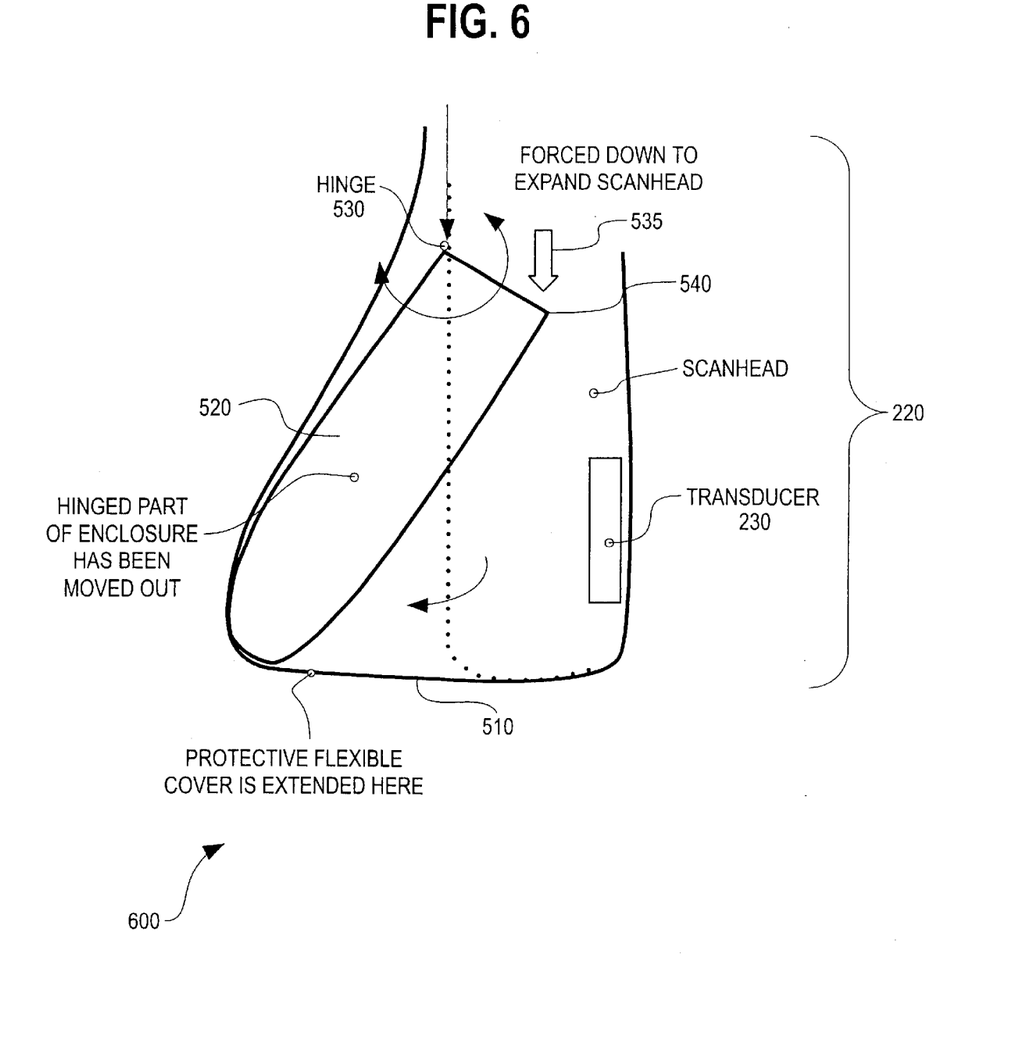
FIG. 6 illustrates a schematic diagram of the operative end of the probe with the scanhead expanded according to an alternative embodiment of the present invention.

FIG. 6 illustrates a schematic diagram of the operative end of the probe with the scanhead 220 expanded according to an alternative embodiment of the present invention. In order to expand the scanhead 220, the engaging shaft 535 is activated via the control handle (not shown). The engaging shaft 535 is preferably a push lever. Alternatively, the engaging shaft 535 may be a threaded shaft attached to the rotating extensor 520 by an engaging nut. As the activation shaft 535 presses down on the force application point 540, the rotating extensor 520 pivots about the hinge 530 and rotates away from the transducer 230. Because the rotating extensor 520 is contained under the flexible cover 510, the flexible cover 510 stretches away from the transducer 230 in response to the movement of the rotating extensor 520. As the rotating extensor 520 pivots on the hinge 530 away from the transducer 230, the scanhead 220 expands.

In order to retract the rotating extensor 520, the engaging shaft 535 is activated s via the control handle (not shown). As the engaging shaft 535 recedes toward the proximal end of the endoscope 210, the rotating extensor 520 pivots on the hinge 530 and follows in response to the movement of the rotating extensor 520. That is, the rotating extensor 520 rotates toward the transducer 230. The flexible cover 510 conforms to the rotating extensor 520. Therefore, as the rotating extensor 520 moves back toward the transducer 230, so to does the flexible cover 510. When the engaging shaft 535 fully retracts within the main body of the endoscope 210, the movement of the rotating extensor 520 is arrested because the rotating extensor 520 comes into contact with the main body of the endoscope 210. This scanhead 220 is fully retracted once the movement of the rotating extensor 520 is arrested by the main body of the endoscope 210.

Alternatively, the extensor may be piston driven. The piston may move in a perpendicular fashion with respect to the main body of the endoscope 210. Thus, as the piston moves away from the main body of the endoscope 210, the extensor moves away from the main body of the endoscope 210 in response to the movement of the piston. Alternatively, the extensor itself may be the piston. Thus, extending the piston expands the scanhead 220; retracting the piston reduces the size of the scanhead 220.

While particular elements, embodiments and applications of the present invention have been shown and described, it is understood that the invention is not limited thereto since modifications may be made by those skilled in the art, particularly in light of the foregoing teaching. It is therefore contemplated by the appended claims to cover such modifications and incorporate those features which come within the spirit and scope of the invention.

What is claimed is:

1. A transesophageal imaging probe including:
an expandable scanhead for improving the positioning of an imaging element mounted on said scanhead, said expandable scanhead expanding to cause at least a portion of said imaging element to contact an esophageal wall of a patient.

2. The probe of claim 1 further including an endoscope that is introduced into the esophagus of a patient wherein said scanhead is located on the distal end of said endoscope.

3. The probe of claim 1 wherein said scanhead includes:
an inflation duct that allows passage of a fluid; and
a flexible pouch that receives said fluid, said scanhead expands when said flexible pouch receives said fluid.

4. The probe of claim 3 wherein said fluid is water.

5. The probe of claim 3 wherein said fluid is air.

6. The probe of claim 1 wherein said scanhead includes an extensor, said extensor operates to expand said scanhead.

7. The probe of claim 1 wherein said scanhead includes:
an extensor, said extensor operates to expand said scanhead; and
a hinge for rotating said extensor.

8. The probe of claim 7 further including a flexible cover that covers said extensor.

9. The probe of claim 6 wherein said extensor is a piston-driven extensor.

10. The probe of claim 1 further including a control handle for allowing control of the expansion of said scanhead.

11. The probe of claim 1 further including a transducer for ultrasonically imaging the internal structures of a patient.

12. The probe of claim 11 wherein said transducer contacts an esophageal wall of a patient as said scanhead expands.

13. The probe of claim 1 wherein said imaging element includes a direction of view, said direction of view is substantially perpendicular to the esophageal wall of a patient.

14. A medical imaging system including:
   a probe for imaging internal structures of a patient, said probe including an expandable scanhead for improving the positioning of an imaging element mounted on said scanhead, said expandable scanhead expanding to cause at least a portion of said imaging element to contact an interior surface of an esophagus of a patient.

15. The system of claim 14 wherein said probe is mounted on an endoscope that is introduced into the esophagus of a patient wherein said scanhead is located on the distal end of said endoscope.

16. The probe of claim 14 wherein said scanhead includes:
   an inflation duct that allows passage of a fluid; and
   a flexible pouch that receives said fluid, said flexible pouch expands when said flexible pouch receives said fluid.

17. The probe of claim 16 wherein said fluid is water.

18. The probe of claim 16 wherein said fluid is air.

19. The probe of claim 14 wherein said scanhead includes an extensor, said extensor operates to expand said scanhead.

20. The probe of claim 14 wherein said scanhead includes:
   an extensor, said extensor operates to expand said scanhead; and
   a hinge for rotating said extensor.

21. The probe of claim 20 further including a flexible cover that covers said extensor.

22. The probe of claim 14 wherein said extensor is a piston that moves away from said scanhead in order to expand said scanhead.

23. The probe of claim 14 further including a control handle for allowing control of the expansion of said scanhead.

24. The probe of claim 14 further including a transducer for ultrasonically imaging the internal structures of a patient.

25. The probe of clam 24 wherein said transducer contacts an esophageal wall of a patient as said scanhead expands.

26. The probe of claim 14 wherein said imaging element includes a direction of view, said direction of view is perpendicular to the esophageal wall of a patient.

27. A method of imaging an internal structure of a patient using an imaging probe having a scanhead including the step of:
   expanding the scanhead of an imaging probe that has been introduced into said patient to improve the positioning of an imaging element, that includes a direction of view, mounted on said scanhead; and
   causing said imaging element to contact an esophageal wall of a patient due to said expanding step.

28. The method of claim 27 wherein said expanding step includes the step of introducing said imaging probe into the esophagus of said patient while said imaging probe is unexpanded.

29. The method of claim 27 including the step of positioning said imaging element substantially parallel to an esophageal wall of said individual.

30. The method of claim 29 wherein said expanding step includes expanding said scanhead after said imaging probe has been positioned to image said internal structure.

31. The method of claim 29 further including the step of positioning said imaging element so that said internal structure is in the direction of view of said imaging element.

32. The method of claim 30 wherein said expanding step includes inflating said scanhead.

33. The method of claim 30 wherein said expanding step includes moving an extensor located in said scanhead.

34. The method of claim 27 further including positioning a transducer mounted on said scanhead.

35. A method of imaging an internal structure of a patient using an imaging probe having a scanhead having an imaging element and an expandable enclosure, said imaging element including a direction of view, said imaging element mounted on a first side of said scanhead, said expandable enclosure mounted on a second side of said scanhead, said method including the step of:
   expanding the scanhead of an imaging probe that has been introduced into an esophagus of a patient to improve the positioning of an imaging element by moving the imaging element into an interior surface of the esophagus so that the direction of view of the imaging element is perpendicular to an internal structure being imaged.

36. An internal imaging probe including an expandable scanhead, said expandable e scanhead including:
   an imaging element mounted on a first side of said scanhead; and
   an expandable enclosure located on a second side of said scanhead, said second side of said scanhead being opposite of said first side of said scanhead, said expandable scanhead expanding through an expansion of said expandable enclosure on said second side of said scanhead causing at least a portion of said imaging element to move into an esophageal wall of a patient.

37. A medical imaging system including:
   probe for imaging internal structures of a patient, said probe including an expandable scanhead for improving the positioning of an imaging element mounted on a first side of said scanhead, said expandable scanhead including an expandable member located on a second side of said scanhead, said second side being opposite of said first side, said expandable scanhead expanding through an expansion of said expandable member on said second side of said scanhead causing at least a portion of said imaging element to move toward an esophageal wall of a patient.

38. A method of imaging an internal structure of a patient using an imagine probe having a scanhead including:
   mounting an imaging element and an expandable member on opposite sides of a scanhead of the imaging probe;
   introducing the scanhead into an esophagus of a patient; and
   expanding the expandable member of the scanhead of an imaging probe that has been introduced into the esophagus of the patient so that the imaging element moves toward a first interior surface of the esophagus and the expandable member moves toward a second interior surface, which is opposite the first interior surface, of the esophagus.

* * * * *